United States Patent [19]

Deinhammer et al.

[11] 4,053,495

[45] Oct. 11, 1977

[54] PROCESS FOR PREPARING METHYLCHLOROSILANES

[75] Inventors: Wolfgang Deinhammer; Volker Frey, both of Burghausen; Manfred Wick, Munich; Rudolf Riedle, Burghausen, all of Germany

[73] Assignee: Consortium fur Elektrochemische Industrie GmbH, Munich, Germany

[21] Appl. No.: 723,871

[22] Filed: Sept. 16, 1976

[30] Foreign Application Priority Data

Oct. 20, 1975 Germany ............................ 2546919

[51] Int. Cl.$^2$ ................................................ C07F 7/12

[52] U.S. Cl. ............................................. 260/448.2 E
[58] Field of Search ................................ 260/448.2 E

[56] References Cited

U.S. PATENT DOCUMENTS 2,802,852  8/1957  George .......................... 260/448.2 E Primary Examiner—Paul F. Shaver

[57] ABSTRACT

An improved process for preparing methylchlorosilanes which comprises reacting tetramethylsilane and hydrogen chloride in the gaseous state with a solid Friedel-Crafts catalyst.

6 Claims, No Drawings

PROCESS FOR PREPARING METHYLCHLOROSILANES

The invention relates to a process for preparing methylchlorosilanes and more particularily to an improved process for preparing methylchlorosilanes in the presence of a solid Friedel-Crafts catalyst.

Heretofore methylchlorosilanes have been prepared by reacting silicon with methyl chloride and the resultant by-product is tetramethylsilane. The tetramethylsilane thus obtained cannot be converted by a simple process into organopolysiloxanes, because it does not contain atoms or groups which are capable of being hydrolyzed or condensed. Therefore, tetramethylsilane has not been used heretofore on an industrial scale to prepare methylchlorosilanes.

Also it is known that methylchlorosilanes can be prepared by reacting tetramethylsilane with hydrogen chloride in the presence of a Friedel-Crafts catalyst, such as aluminum chloride or ferric chloride. (U.S. Pat. No. 2,802,852 to George).

This process can be illustrated by the following equation:

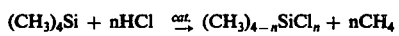

$$(CH_3)_4Si + nHCl \rightleftharpoons (CH_3)_{4-n}SiCl_n + nCH_4$$

In this equation, $n = 1$ or 2. Thus, the methylchlorosilanes which can be prepared by reacting tetramethylsilane with hydrogen chloride are trimethylchlorosilane and/or dimethyldichlorosilane. Both of these methylchlorosilanes are in demand, although in varying ratios to one another. Trimethylchlorosilane, and its derivatives for example, may be used to treat inorganic substances, such as silicon dioxide fillers, or organic substances to render them hydrophobic or for the introduction of endblocking units into organopolysiloxane chains. The dimethyldichlorosilanes can be hydrolyzed to form dimethylpolysiloxanes which are the most important starting material for the preparation of organopolysiloxane elastomers and oils.

Also, in the process described in U.S. Pat. No. 2,802,852, at least part of the reaction components must be maintained in a liquid state and the catalyst is dissolved in the reaction mixture.

In the process of this invention, the methylchlorosilanes are trimethylchlorosilane and dimethyldichlorosilane. Furthermore, the process of this invention has certain advantages over that described in U.S. Pat. No. 2,802,852. For example, higher yields of the desired methylchlorosilanes are obtained. Also, the process of this invention can be carried out at a substantially lower cost when compared with the expenditure required for the continuous method known in the art.

Therefore, it is an object of this invention to provide an improved process for preparing methylchlorosilanes. Another object of this invention is to provide an improved process for preparing methylchlorosilanes from tetramethylsilane. Still another object of this invention is to provide an improved process for preparing methylchlorosilanes in the presence of a solid Friedel-Crafts catalyst. A further object of this invention is to provide an improved process for preparing methylchlorosilanes having improved yields with greater selectivity.

The foregoing objects and others which will become apparent from the following description are accomplished in accordance with this invention, generally speaking, by providing an improved process for preparing methylchlorosilanes which comprises passing tetramethylsilane and hydrogen chloride in a gaseous form over or through a solid Friedel-Crafts catalyst.

In the process of this invention, both tetramethylsilane and hydrogen chloride are employed in a gaseous state.

The tetramethylsilane may be used alone or in admixture with other gases. It is preferable, however, to pass over or through the Friedel-Crafts catalyst a gaseous mixture containing at least 50 percent by weight of tetramethylsilane, excluding hydrogen chloride, or to use as tetramethylsilane the gaseous mixture of the by-products boiling at 20° to 30° C which are obtained during the preparation of methylchlorosilanes from silicon and methyl chloride.

From 0.1 to 5 mols of hydrogen chloride are preferably used per mol of tetramethylsilane.

If the methylchlorosilane required is trimethylchlorosilane, from 0.1 to 1.1 mols, preferably 0.9 to 1.05 mols, of hydrogen chloride are used per mol of tetramethylsilane.

When the methylchlorosilane required is dimethyldichlorosilane, from 1.2 to 5 mols, preferably 2 to 4 mols, of hydrogen chloride are used per mol of tetramethylsilane.

While the ratio between the amount of dimethyldichlorosilane and the amount of trimethylchlorosilane can be regulated only to a limited extent and/or at a great cost in the preparation of methylchlorosilanes by reacting silicon with methyl chloride, it is possible with the process of this invention to alter the production of dimethyldichlorosilane and trimethylchlorosilane to the changing demand for these two silanes, simply by changing the ratio of hydrogen chloride to tetramethylsilane.

The expression "solid Friedel-Crafts catalyst" as used herein provides that the Friedel-Crafts catalyst is used in solid form, and not in either liquid or dissolved form. The Friedel-Crafts catalyst is moreover preferably dry, i.e., it is not surrounded by or enveloped in a liquid.

The Friedel-Crafts catalysts which are preferred are aluminum chloride ($AlCl_3$) and/or ferric chloride ($FeCl_3$). The grain size of the Friedel-Crafts catalysts is preferably from 0.1 to 10 mm (diameter). The Friedel-Crafts catalysts may be precipitated on an inert catalyst carrier, such as silica gel, aluminum hydroxide, aluminum oxide or silicates. The proportion of the sum of the weight of Friedel-Crafts catalyst and the weight of inert catalyst carrier to the total weight of these substances and any other solid substances which might be mixed with the Friedel-Crafts catalyst is preferably at least 90 percent by weight. The catalyst may be in the form of a solid bed or as a fluidized bed.

The temperature at which the process of this invention is carried out is preferably from 30° to 150° C, and more preferably from 60° to 120° C.

The process of this invention is preferably carried out at the pressure of the surrounding atmosphere, i.e., at 760 mm Hg (abs.) or approx. at 760 mm Hg (abs.). If desired, however, higher or lower pressures may also be used.

The contact time of the reaction components are reaction products in or over the Friedel-Crafts catalyst is preferably from 1 to 100 seconds, and more preferably from 5 to 50 seconds.

The yields obtained with the process of this invention are generally from 70 to 100 mol percent, based in each case on the reaction component used in the smallest quantity. The selectivities may range from 80 to 95 percent for trimethylchlorosilane and from 80 to 100 percent for dimethyldichlorosilane. It is surprising that with the relatively short contact times indicated above, the yields are extremely high. Moreover, the process of this invention as compared with the process of U.S. Pat. No. 2,802,852, can be carried out continuously on a large scale in a simple apparatus. In comparison with the process of U.S. Pat. No. 2,802,852, the expenditure required for condensing the low-boiling tetramethylsilane before reaction with hydrogen chloride, the use of pressure or expensive cooling equipment in order to maintain the tetramethylsilane in liquid form, and replacement and/or recovery of the catalyst which is dissolved in the reaction product is eliminated by the process of this invention.

The reaction products obtained by the process of this invention may simply be distilled together with the methylchlorosilanes obtained by reacting silicon with methyl chloride. Unreacted tetramethylsilane and unreacted hydrogen chloride can be recycled through the process of this invention.

In the examples all parts are by weight unless otherwise specified.

EXAMPLE 1

Hydrogen chloride which has been saturated at 9° C with tetramethylsilane (molar ratio of tetramethylsilane/HCl = 1 : 0.97) is introduced at 80° C into the bottom of a vertical glass tube which can be heated, has an internal diameter of 1 cm and a length of 40 cm, and is filled with coarse-grained $AlCl_3$. The gases emerging from the top of the tube are condensed. After 3.5 hours, 40.2 parts of tetramethylsilane have been introduced into the tube. The dwell time of the reaction components and reaction products is about 20 seconds. From the condensed gases 49.3 parts of distillate are obtained, which consists of 10 percent by weight of tetramethylsilane, 78 percent by weight of trimethylchlorosilane and 12 percent by weight of dimethyldichlorosilane. This corresponds to a yield of about 88 mol percent, based on the tetramethylsilane used, and a selectivity of 89 percent for trimethylchlorosilane.

EXAMPLE 2

Hydrogen chloride which has been saturated at 8° C with tetramethylsilane (molar ratio of tetramethylsilane/HCl = 1 : 1.03) is introduced at 90° C into the bottom of a vertical glass tube which can be heated, has an internal diameter of 1 cm and a length of 40 cm., and is filled with coarse-grained $FeCl_3$. The gases emerging from the top of the tube are condensed. After 5 hours, 42.1 parts of tetramethylsilane have been introduced into the tube; the dwell time of the reaction components and reaction products is about 26 seconds. Based on the tetramethylsilane introduced into the tube, about 72 mol percent has reacted, with a selectivity of 95 percent for trimethylchlorosilane.

EXAMPLE 3

Hydrogen chloride which has been saturated at −2° C with tetramethylsilane (molar ratio of tetramethylsilane/HCl = 1 : 2.1) is introduced at 90° C into the bottom of a vertical glass tube which can be heated, has an internal diameter of 1 cm and a length of 40 cm, and is filled with coarse-grained $AlCl_3$. After 3 hours, 20.5 parts of tetramethylsilane have been introduced into the tube. The dwell time of the reaction components and reaction products is about 22 seconds. Based on the tetramethylsilane introduced into the tube, 100 mol percent has reacted with a selectivity of 83 percent for dimethyldichlorosilane and 16 percent for trimethylchlorosilane.

What we claim is:

1. An improved process for preparing methylchlorosilanes by reacting tetramethylsilane with hydrogen chloride in the presence of a Friedel-Crafts catalyst, the improvement which comprises contacting tetramethylsilane with hydrogen chloride in a gaseous state with a solid Friedel-Crafts catalyst for from 1 to 100 seconds.

2. The improved process of claim 1, wherein from 0.1 to 1.1 mols of hydrogen chloride are used per mol of tetramethylsilane.

3. The improved process of claim 1, wherein from 1.2 to 5 mols of hydrogen chloride are used per mol of tetramethylsilane.

4. The improved process of claim 1 wherein the Friedel-Crafts catalyst is selected from the class consisting of aluminum chloride, ferric chloride and mixtures thereof.

5. The improved process of claim 1 wherein the temperature is from 60° to 120° C.

6. The improved process of claim 1 wherein the contact time of the reaction components and the reaction products, with the Friedel-Crafts catalyst is from 5 to 50 seconds.

* * * * *